United States Patent [19]

Ross et al.

[11] Patent Number: 5,220,006
[45] Date of Patent: Jun. 15, 1993

[54] IDENTIFICATION OF A SUPPRESSOR OF ATHEROGENIC APOLIPOPROTEIN

[75] Inventors: Robert S. Ross; Andrew C. Li; Jeffrey M. Hoeg; H. Bryan Brewer, all of Bethesda, Md.

[73] Assignee: The United States of America as represented by the Department of Health and Human Services, Washington, D.C.

[21] Appl. No.: 601,931

[22] Filed: Oct. 23, 1990

[51] Int. Cl.$^5$ .................... C07H 15/12; C07H 17/00; C12Q 1/68
[52] U.S. Cl. ........................ 536/24.1; 435/6; 435/69.1; 435/69.6; 435/172.3; 436/71
[58] Field of Search .................. 435/172.3, 69.1, 69.6, 435/6; 436/71; 536/27

[56] References Cited

PUBLICATIONS

Carlsson et al. "Negative and Positive Promoter Elements . . . " *Gene*, 77 (1989) 113–121.
Das et al. "Cell Type-Specific Expression of the Human . . . " *J. Biol. Chem.*, Aug. 15, 1988 263:23 pp. 11452–11458.

*Primary Examiner*—Robert A. Wax
*Assistant Examiner*—Hyosuk Kim
*Attorney, Agent, or Firm*—Foley & Lardner

[57] ABSTRACT

A region in the apolipoprotein B gene has been identified that suppresses the transcription of apolipoprotein B. Polypeptides that bind to the suppressor region have been isolated.

2 Claims, 7 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA (xi) SEQUENCE DESCRIPTION: SEQ ID NO:1:

GCAAATCCAA GGTCCACCAA AATGGAAAAG A                                31

(2) INFORMATION FOR SEQ ID NO:2:

(i) SEQUENCE CHARACTERISTICS:
(A) LENGTH: 25 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA (xi) SEQUENCE DESCRIPTION: SEQ ID NO:2:

CAAGGTCCAC CAAAATGGAA AAGAA                                       25

(2) INFORMATION FOR SEQ ID NO:3:

(i) SEQUENCE CHARACTERISTICS:
(A) LENGTH: 26 base pairs
(B) TYPE: nucleic acid
(C) STRANDEDNESS: double
(D) TOPOLOGY: linear (ii) MOLECULE TYPE: Other nucleic acid;
(A) DESCRIPTION: Synthetic DNA (xi) SEQUENCE DESCRIPTION: SEQ ID NO:3:

CACGTCTCCA CCAAGACAGC GCTCAG                                      26

IDENTIFICATION OF A SUPPRESSOR OF ATHEROGENIC APOLIPOPROTEIN

The present invention is related generally to the identification and characterization of new genes. More particularly, the present invention is related to the identification of a region in the apolipoprotein B gene that suppresses the transcription of atherogenic apolipoprotein B (apoB).

BACKGROUND OF THE INVENTION

Atherosclerotic coronary artery disease (CAD) is one of the leading causes of mortality in the United States. Multiple epidemiologic studies have shown plasma levels of certain lipoproteins and their associated apolipoprotein moieties to be highly correlated with increased risk for development of CAD (The Expert Panel, 1988, *Arch. Int. Med.* 148:36-69; Kottke et al, 1986, *Mayo Clinic Proceedings* 61:313-320; Hoefler et al, 1988, *Arteriosclerosis* 8:398-401). Specifically, increased concentrations of low density lipoprotein (LDL), apoB, and lipoprotein Lp(a) as well as decreased high-density lipoproteins (HDL) and apoAI concentrations, have been implicated as risk stratifiers for development of premature atherosclerotic disease (Gordon et al, 1981, *Arch. Intern. Med.* 141:1128-31; Castelli et al, 1977, *Circulation* 55:767-772; Kottke et al, supra; Hoefler et al, supra). Therapeutic modalities presently exist that enable appropriate modulation of LDL and HDL metabolism, but therapy has not been specifically directed toward transcriptional regulation of the apolipoproteins.

ApoB is the product of a 43 kb gene residing on chromosome 2, which is composed of 29 exons and 28 introns (Ludwig et al, 1987, *DNA* 6:363-372). Transcription occurs in liver and intestine to produce a 14.1 kb mRNA. Regulation of apoB gene expression is achieved through a unique RNA editing mechanism; nucleotide 6666 can undergo a C to U substitution resulting in formation of a stop codon at this location in the transcript (Powell et al, 1987, *Cell* 50:831-840; Chen et al, 1987, *Science* 238:363-366; Higuchi et al, 1988, *Proc. Natl. Acad. Sci. USA* 85:1772-1776). Therefore, a single transcript can produce two isoproteins of 512 and 250 kDa, designated apoB-100 and apoB-48 respectively. Regulation of apoB at the transcriptional level has been only recently investigated (Das et al, 1988, *J. Biol. Chem.* 263:11452-11458; Carlsson and Bjursell, 1989, *Gene* 77:113-121; Levy-Wilson and Fortier, 1989, *J. Biol. Chem.* 264:9891-9896).

However, a factor, element or domain which suppresses the transcription of apoB has not heretofore been known or described.

SUMMARY OF THE INVENTION

It is, therefore, an object of the present invention to provide a specific nucleotide sequence that suppresses the transcription of atherogenic apolipoprotein.

It is a further object of the present invention to provide isolated, biologically substantially pure polypeptides involved in the transcriptional regulation of the apoB suppressor gene.

It is another object of the present invention to control the synthesis of atherogenic apolipoprotein B.

It is an additional object of the present invention to provide modulators of apoB suppressor gene.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows apoB 5' deletional constructs and their relative transcriptional activity in Hep G2 cells. Schematic representations of the constructs containing progressive deletions of the 5' flanking sequence of the apoB gene that were placed upstream of the chloramphenicol acetyltransferase gene (CAT gene) are depicted in the panel on the left. The location in base pairs relative to the apoB transcriptional start site is indicated by the numbers under each construct. The right panel contains an autoradiograph of the thin layer chromatography plate illustrating the ability of extracts of Hep G2 cells transfected with the constructs displayed in the left hand panel to acetylate chloramphenicol. The left row of the thin layer autoradiograph represents the amount of unacylated chloramphenicol, the middle row the amount of monoacylated chloramphenicol and the right row the amount of diacylated chloramphenicol.

FIG. 5 demonstrates the repression of the transcriptional activity of a heterologous promoter by the apolipoprotein B upstream suppressor (aBUSS) sequence. Panel A schematically summarizes the plasmid constructs utilized in the apoB/hsv-tk/CAT heterologous promoter/reporter studies. All plasmids utilized BLCAT2 (A) as the parent construct. This construct contained the minimal thymidine kinase (TK) promoter just upstream of the chloramphenicol acetyltransferase (CAT) gene. Constructs containing the 25 base pair apoB sequence (-449 to -425) was placed upstream of the TK promoter as either single (B,D,E,F) or duplicate (C) motifs. Constructions were placed in either the correct (B,C,E) or the reverse (D,F) orientation as shown by the arrows. Constructs E and F contained the larger apoB region -514 to -385. Panel B summarizes the relative CAT activity of the apoB/hsv-tk/CAT constructs for the respective constructs outlined in panel A in transfected Hep G2 (open bars) and Caco-2 (hatched bars). Histograms shown the average +/− standard error of the mean of quadruplicate studies. CAT activity of each experiment was normalized to that of the base vector, BLCAT2.

DETAILED DESCRIPTION OF THE INVENTION

The above and various other objects and advantages of the present invention are achieved by a cloned 31 base pair element in the apoB 5' flanking region which binds two proteins of about 23.5 and 25.4 kDa and decreases apoB transcription. The cloned suppressor element has the following nucleotide sequence (SEQ ID NO: 1)

GCAAATCCAAGGTCCACCAAAATG-
GAAAAGA.

Of course, the double stranded nucleic acid will have a second sequence complementary to the sequence shown above.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially pure" as used herein means as pure as can be obtained by standard isolation and purification techniques.

The abbreviations used herein include the following: aBUSS, apoB upstream suppressor site; apo, apolipoprotein; ARP, apoB repressor protein; CAD, coronary artery disease; CAT, chloramphenicol acetyltransferase; HDL, high density lipoproteins; HSV, herpes simplex virus; LDL, low density lipoproteins; Lp(a), lipoprotein Lp(a); PCR, polymerase chain reaction; tk, thymidine kinase.

MATERIALS AND METHODS

Materials

[32P] ATP (>9000 Ci mMol) was obtained from New England Nuclear (Wilmington, DE). Restriction enzymes, T4 polynucleotide kinase and calf-intestinal alkaline phosphatase were obtained from Bethesda Research Labs, Inc. (Gaithersberg, MD), New England Biolabs (Beverly, MA), or Boerhinger-Mannheim Biochemicals (Indianapolis, IN). Exonuclease III and mung bean exonuclease were from Promega Corp. (Madison, WI). Poly [(dA-dT)-(dA-dT)] was supplied by Sigma Chemical Co. (St. Louis, MO). DNAse I was obtained from Pharmacia-LKB, Inc. (Piscataway, NJ). pBLCAT2 and pBLCAT3 plasmids were obtained from the American Type Culture Collection (Rockville, MD). Oligonucleotides were synthesized on an Applied Biosystems (Foster City, CA) Model 380B DNA synthesizer using standard phosphoramidite chemistry. PCR products were synthesized using reagents in the GeneAmp ™ kit in a DNA Thermal Cycler purchased from Perkin-Elmer Cetus, Corp. (Norwalk, CT). Luciferin was obtained from Analytical Luminescence, Inc. (San Diego, CA).

Plasmid Constructions

Standard techniques were used for all cloning procedures and plasmid isolations (Maniatis et al, 1982, Molecular cloning: a laboratory manual. Cold Spring Harbor Laboratory, Cold Spring Harbor, NY. 1-545). The parent plasmid (pNLBCAT), from which all 5' to 3' deletions of the apoB regulatory unit were derived, has been previously described (Ross et al, 1989, *Biochem. Biophys. Acta.* 1004:29–35). Deletions were constructed by using convenient restriction enzyme sites in the pNLBCAT clone or by restriction enzyme digestion followed by exonuclease III/mung bean nuclease digestions utilizing protocols as recommended by the manufacturer. The 5' site of the apoB regulatory region was confirmed in each deletional mutant by dideoxy sequencing (Sanger et al, 1977, *Proc. Natl. Acad. Sci. USA* 74:5463–5467).

The promoterless chloramphenicol acetyltransferase (CAT) plasmid pSVOCAT and pRSVCAT containing the Rous sarcoma virus (RSV) LTR were utilized as negative and positive controls respectively for all CAT transfection studies (Gorman et al, 1982, *Mol. Cell. Biol.* 2:1044–1051; Gorman et al, 1982, *Proc. Natl. Acad. Sci. USA* 79:6777–6781). pRSVL in which the RSV LTR controls the luciferase gene was utilized to control for transfection efficiency (DeWet et al, 1987, *Mol. Cell. Biol.* 7:525–537). In order to evaluate the effects of putative apoB regulatory elements, plasmid pBLCAT2 (ATCC# 37527) containing the Herpes Simplex Virus (HSV) thymidine kinase (tk) linker scanning mutant LS-115/-105 controlling the CAT gene was used (Luckow and Schutz, 1987, *Nuc. Acids Res.* 15:5490). Double-stranded apoB oligonucleotides were ligated into the unique BamHI site in pBLCAT2. In addition, when longer regions of the apoB 5' flanking region were to be utilized as regulatory elements, these regions were amplified using the polymerase chain reaction (PCR) and cloned into pBLCAT2. All insert sequences were confirmed with chain termination sequencing. pBLCAT3 (ATCC# 37528), a promoterless CAT plasmid which is identical to pBLCAT2 except for the HSV tk sequence, was used as a negative control plasmid in all pBLCAT2 studies.

Transfection studies, CAT and Luciferase assays

Transient transfection studies were performed via the calcium phosphate co-precipitation technique (Ross et al, supra). 15 μg of pNLBCAT and its truncated mutants were used in all studies along with 20 μg of carrier tRNA. pRSVL (5 μg) was co-transfected to control for transfection efficiency. Studies utilizing pBLCAT2 and its derivatives utilized 10 μg of CAT containing plasmids.

CAT and luciferase assays were performed as reported by Rosenthal (1987, In Methods in Enzymology. S. L. Berger and A. R. Kimmel, editors. Academic Press, Inc. Vol. 152:704–720) and Mercola et al (1985, *Science* 227:266–270). Protein concentrations were measured on all cellular extracts by the method of Bradford (1976, *Anal. Biochem.* 27:248–254). Studies were performed in cell lines known to produce apoB (Hep G2, a human hepatoma line, ATCC HB8065; and Caco-2 a colonic carcinoma line, ATCC HTB37) as well as control, non-apoB producing lines including KB, an epithelial carcinoma cell line (ATCC CCL17), NIH3T3 fibroblasts, and chinese hamster ovary (CHO) cells.

Radiolabeling of DNA fragments

DNA fragments to be used as probes were radiolabeled as follows. Oligonucleotides (20 bp) were chosen at the 5' ends of the coding and non-coding strands of the desired region of the apoB 5' flanking sequence to be labeled. The oligonucleotides were then end-labeled with [$^{32}$P] dATP and T4-polynucleotide kinase using standard procedures (Maniatis et al, supra). Labeled oligonucleotides were isolated from free nucleotide using a G-25 Sephadex spin-column and then ethanol precipitated. The labeled oligonucleotide was then utilized as one of two primers in the PCR to generate the appropriate DNA fragment. The labeled DNA fragment was evaluated for the correct size and then isolated by preparative polyacrylamide gel electrophoresis and subsequent gel purification. All fragments were further evaluated as to sequence specificity using chemical cleavage DNA sequencing methods (Maxam and Gilbert, 1977, *PNAS. USA* 74:560–564).

Nuclear extract preparation, gel retardation and DNAse I footprinting assays

Nuclear extracts from Hep G2, Caco-2, and KB cells were prepared by the method of Dignam (Dignam et al, 1983, *Nuc. Acids Res.* 11:1475–1489) and stored in liquid nitrogen until use. Gel mobility shift assays were performed using the method of Strauss and Varshavsky (1984, *Cell* 37:889–901) utilizing 3-5 μg of poly [dA-dT)-(dAdTO] as non-specific competitor DNA. DNAse I footprinting reactions were performed by the technique of Petty et al, 1989, *J. Biol. Chem*. In press.

Southwestern Blotting

Southwestern blotting was performed by the method of Schreiber et al (1988, *EMBO J.* 7:4221–4229) utilizing endlabeled double-stranded apoB oligonucleotides as probes.

DNA Sequence analysis

DNA sequence analysis was carried out using the Fasta program on the Bionet National Computer Resource.

RESULTS

Figure 1:
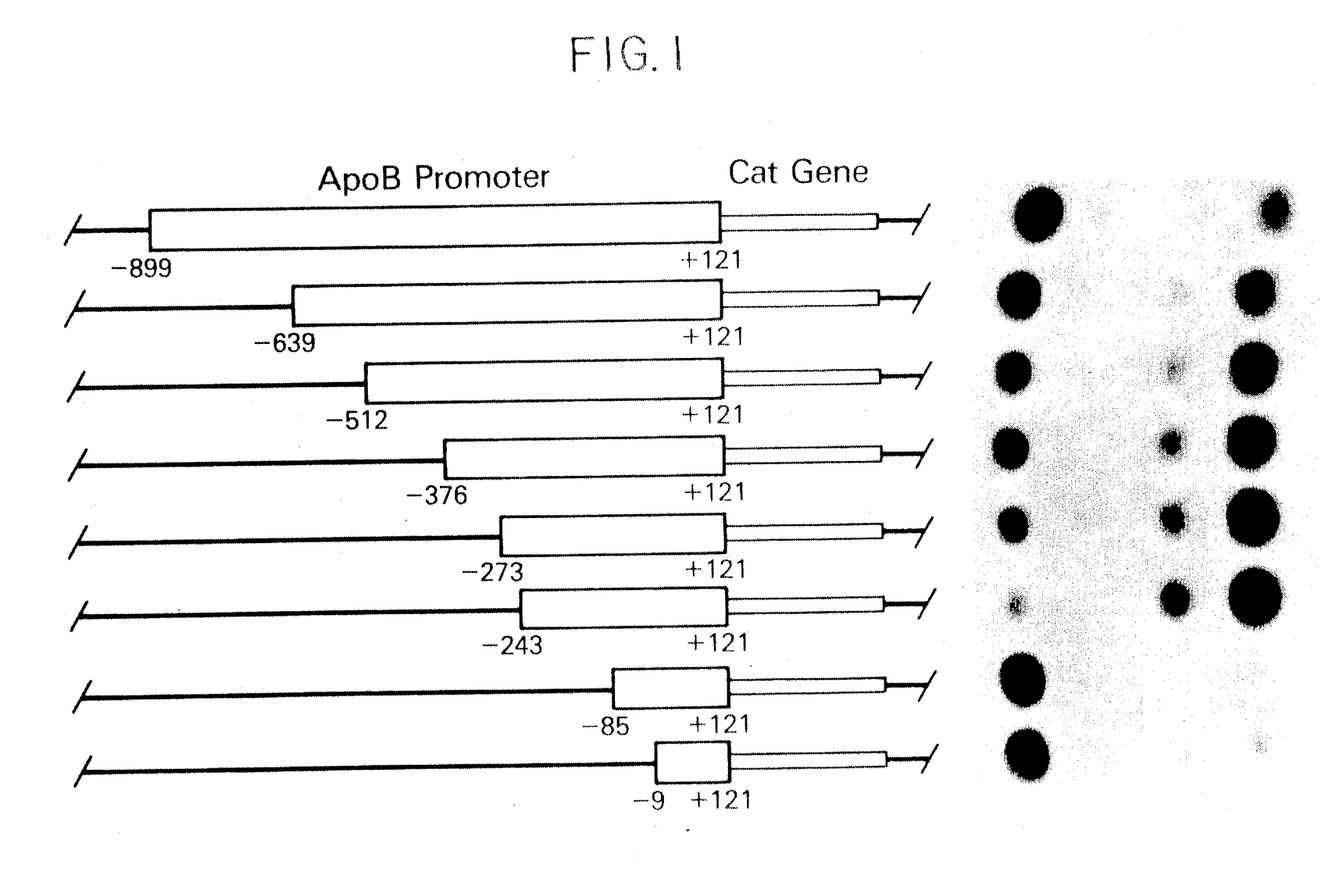
Figure 2:
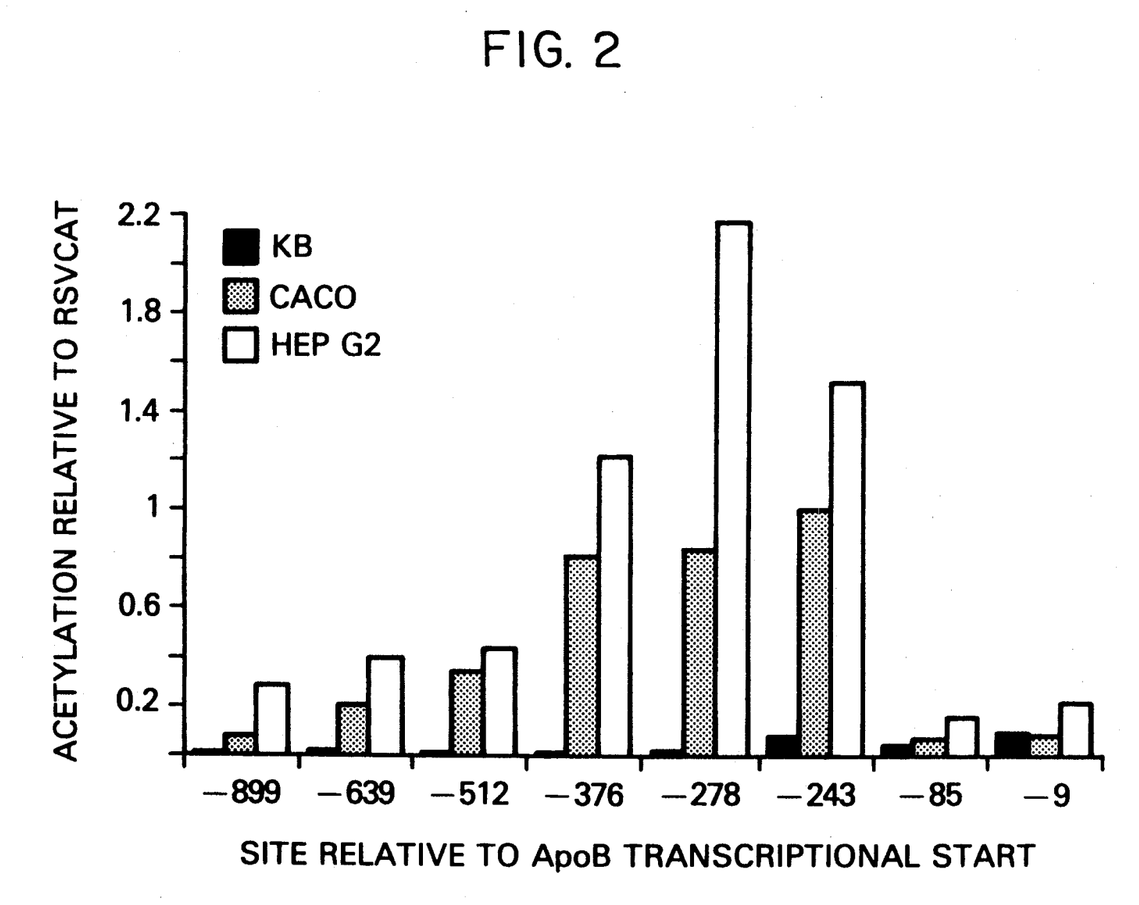
FIG. 2 shows the relative chloramphenicol acetyltransferase (CAT) activity of 5' deletional mutants transfected into Hep G2, Caco-2 and KB cells. Deletional mutants of the apoB 5' flanking sequence were transfected into cell lines that synthesized (Hep G2 and Caco-2) or did not (KB) synthesize apoB. The ability of cellular extracts to acetylate chloramphenicol was determined and compared to the positive RSVCAT control. Each CAT activity was normalized for transfection efficiency and the cell protein. Each bar represents at least 3 separate experiments with transfections of each deletional mutant within each experiment.

Regulatory domains in the 5' flanking sequence of the apoB gene were initially identified by evaluation of relative transcriptional activity of 5' deletional mutants in transient transfection studies (FIG. 1). Initial studies of the plasmid containing 899 bp of the 5' flanking region of the apoB gene showed CAT activity in Hep G2 and Caco-2 lines, however no activity was detected in the non-apoB producing lines CHO, KB or 3T3 (data not shown). Deletional analyses revealed areas important for negative as well as positive regulation (FIG. 2). Progressive deletion of the region from -899 to -278 from the apoB transcriptional start site resulted in significant tissue-specific increases in CAT activity from 5 to 8 times that of baseline. This effect was not noted in KB cells which do not synthesize apoB. Further deletion of the region from -278 to -85 resulted in a reduction in activity to baseline indicating that this region contains important apoB positive control elements. Deletion of the region downstream of -278 allowed moderate expression in the KB control cells. Therefore, elements upstream of this region must help confer apoB promoter tissue specificity.

Figure 3:
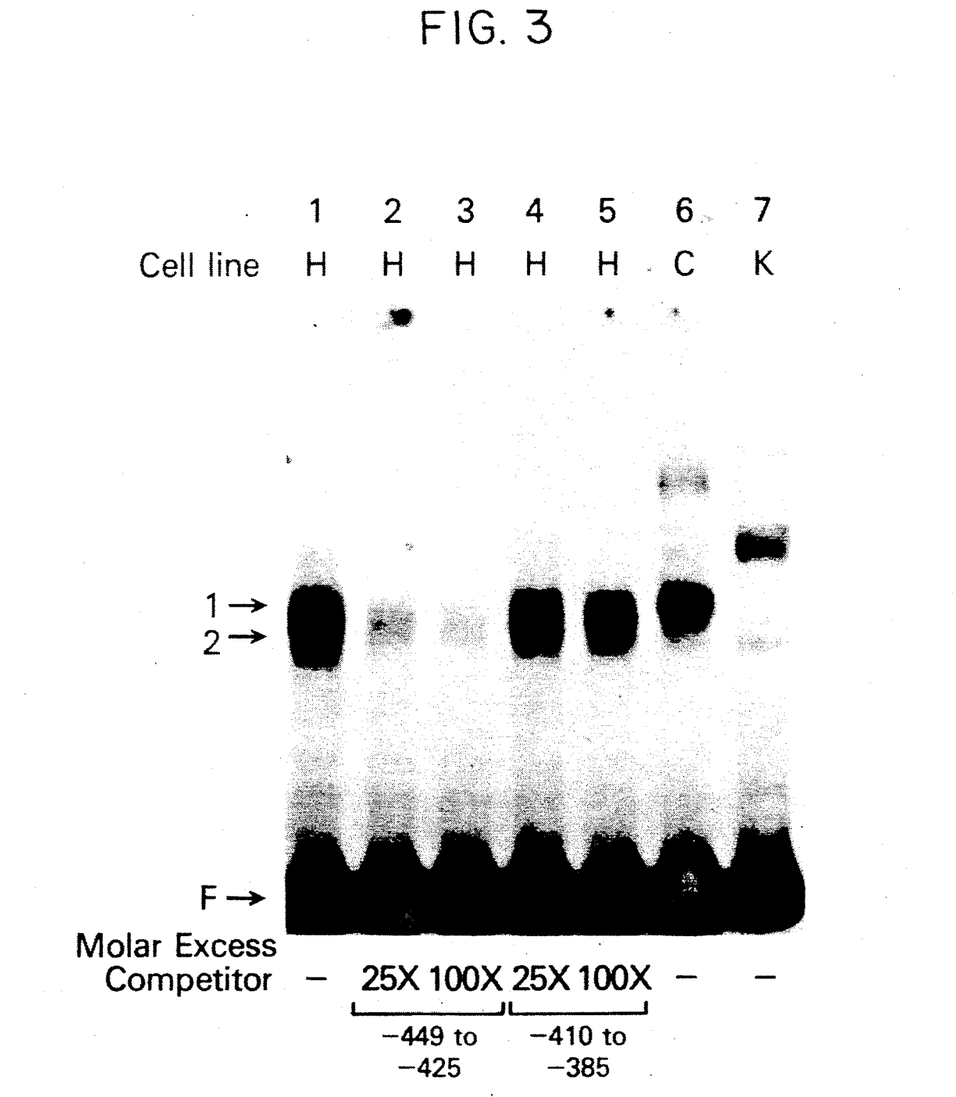
FIG. 3 demonstrates the gel mobility shift assessment of apoB constructs using nuclear extracts isolated from Hep G2, Caco-2, and KB cells. The end-labeled apoB fragment from -509 to -385 was incubated in the presence of 5 ug of Hep G2 (H), Caco-2 (C) or KB (K) nuclear extracts. Incubations with the probe were conducted either with or without 25 and 100 fold molar excesses of double stranded oligonucleotide competitors. Sequences of these double stranded oligonucleotides are identified as the position relative to the apoB transcriptional start site.
Figure 4:
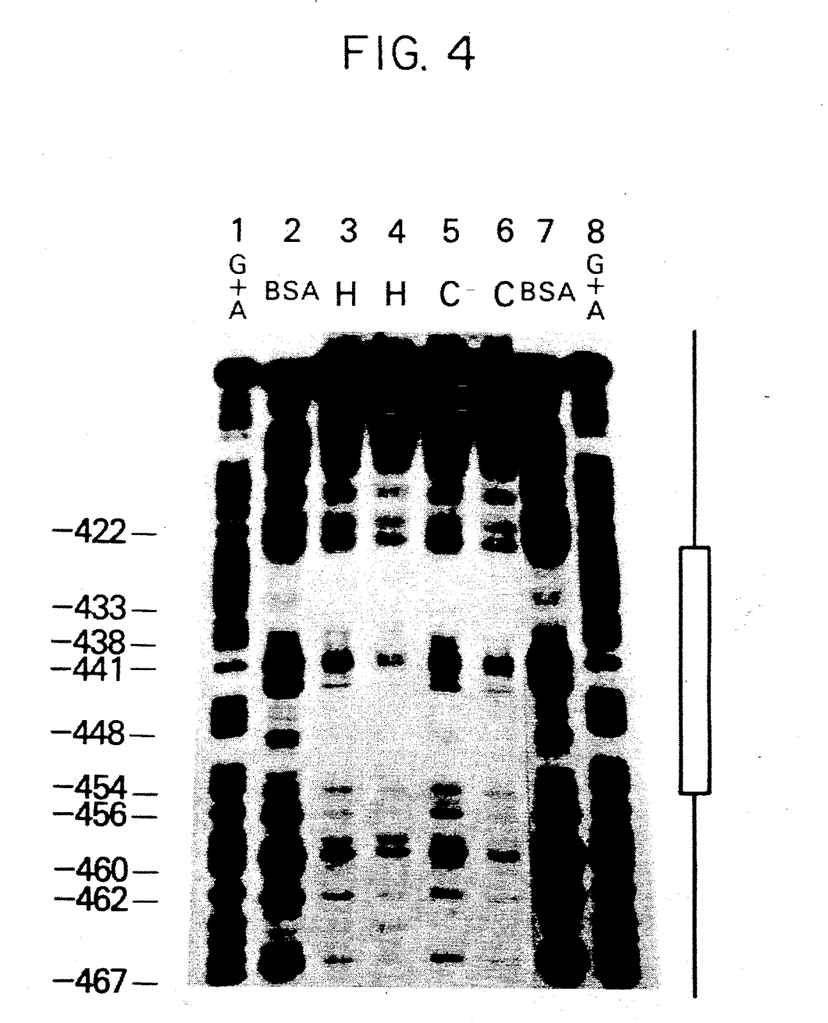
FIG. 4 shows the results of DNAseI protection assay of apoB (-509 to -385) utilizing nuclear extracts from Hep G2 and Caco-2 cells. Nuclear extracts were incubated with the 5' end-labeled probe, and sequence analysis was undertaken after a DNAse I digestion. Lanes 1 and 8 depict MaxamGilbert G+A sequencing reactions performed in the absence of nuclear extract preincubation, and lanes 2 and 7 represent the sequence analysis after an initial incubation using 10 ug of bovine serum albumin. Lanes 3 and 4 utilized 30 and 60 ug of crude Hep G2 (H) nuclear extract, respectively, and lanes 5 and 6 represent 30 and 60 ug of crude Caco-2 nuclear extract. The numbers on the left of the figure indicate the position relative to the apoB transcriptional start site. The region of protection is shown schematically to the right of the sequencing (G+A) gel.

Gel mobility shift assays were performed in order to assess the apoB negative regulatory region for nuclear protein binding. A sequence of the apoB regulatory region was chosen as a probe for the mobility shift assay, which contained important negative regulatory elements based on the transient transfection studies (FIG. 2). When the region from -509 to -385 was incubated with nuclear extracts from Hep G2, Caco-2, and KB cells, unique gel shift bands were detected in the apoB producing cells (FIG. 3). Two unique bands could be discerned in the Hep G2 extract, whereas only the upper one of these bands was detected in the Caco-2 extract (FIG. 3). These gel shift bands were competed by molar excesses of an unlabeled double-stranded oligonucleotide covering the region from -449 to -425 (SEQ ID No: 2) (CAA GGT CCA CCA AAA TGG AAA AGA A) in the apoB regulatory region. However, other oligonucleotides from an unrelated apoB sequence, such as -410 to -385 (SEQ ID No: 3) (CAC GTC TCC ACC AAG ACA GCG CTC AG) did not compete for the labeled probe or for protein binding. Similar results were found with Caco-2 nuclear extracts in gel mobility shift assays (data not shown). DNAse I footprinting assays were performed to further delineate the region in the apoB 5' flanking sequence to which these proteins bind. When incubated with the unfractionated nuclear extracts as utilized in the gel mobility shift assays, a distinct footprint was identified with Hep G2 and Caco-2 extracts in the region -456 to -426 (FIG. 4). This protected region was identical with both Hep G2 and Caco-2 nuclear extracts and agrees with the data obtained from competition studies using the gel retardation assay. The 5' flanking region of apoB which binds to these proteins has been designated herein as aBUSS.

Figure 5A:
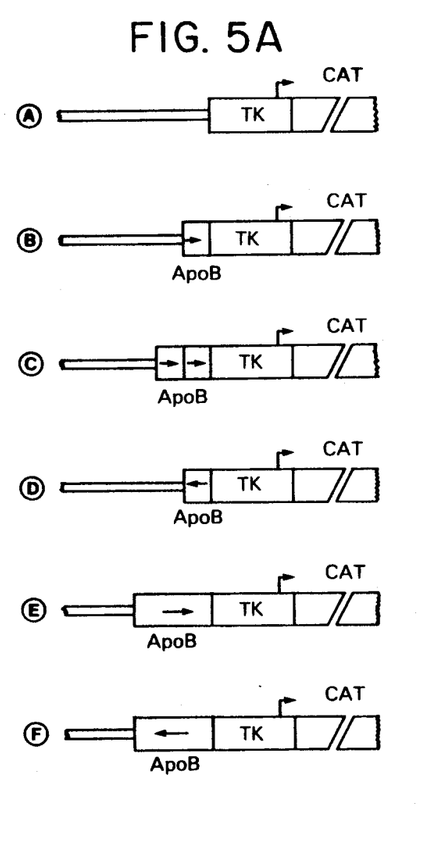
Figure 5B:
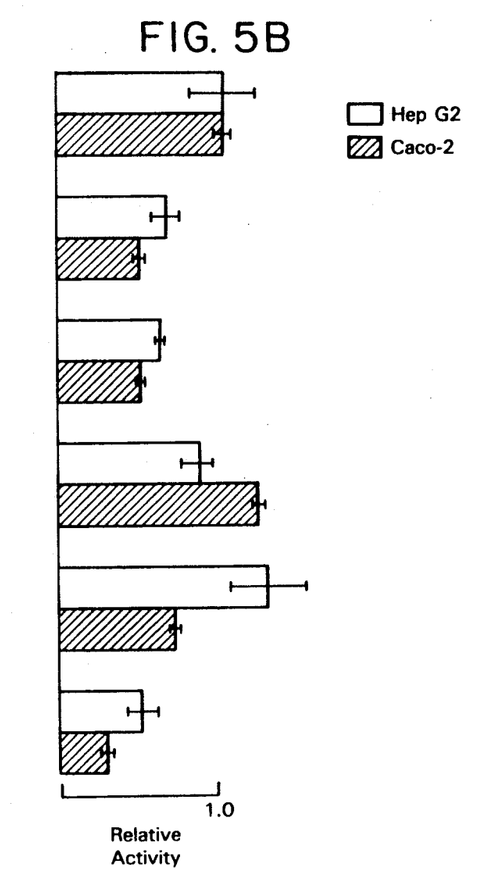

The functional significance of this sequence motif in the apoB 5′ flanking region was evaluated. Experiments were initiated using pBLCAT2, a vector containing the hsv/tk linker scanning mutant -115/-105 of McKnight, as the base construct (McKnight and Kingsbury, 1982, Science 217:316-325). Double-stranded oligonucleotides or PCR amplified products corresponding to various regions of the apoB 5′ flanking sequence or irrelevant sequences were synthesized and then cloned upstream of the hsv/tk promoter. Transient transfection studies were performed with these plasmids in Hep G2 and Caco-2 cell lines. The apoB sequence from -449 to -425, a dimer of this sequence, the PCR amplified apoB region from -514 to -385, and similarly sized control/irrelevant sequences were utilized as synthetic regulatory elements in these studies (FIG. 5). Both the monomeric and dimeric apoB oligonucleotide units effected a significant reduction in CAT activity relative to baseline when they were positioned in the correct orientation relative to the transcriptional start site (FIG. 5B, C). Suppression over baseline was not significant when these elements were placed in reverse orientation (FIG. 5D). In order to assess the influence of flanking sequences from the native apoB promoter on the aBUSS site, a region from -514 to -385 from apoB transcriptional start site was synthesized using the PCR. This sequence was then cloned in both orientations upstream of the hsv/tk promoter in BLCAT2. Relative activities of these constructs, as compared to baseline tk-CAT, revealed significant suppression of activity with the reverse, but not correctly positioned region (FIGS. 5E, F). No repression over baseline was noted when control/irrelevant sequences were placed in similar upstream positions relative to the has/tk promoter.

Figure 6:
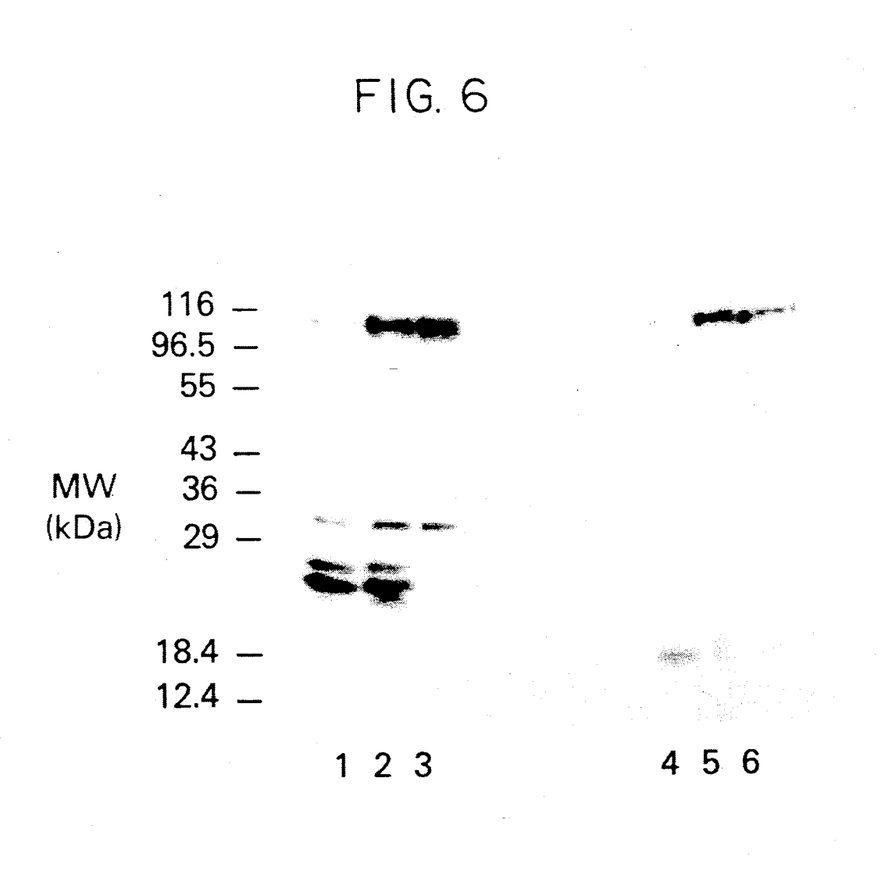
FIG. 6 shows the results of Southwestern blot of nuclear extracts from Hep G2, Caco-2, and KB cells utilizing radiolabeled oligonucleotides. Nuclear extracts from Hep G2 (lanes 1,4), Caco-2 (lanes 2,5), and KB (lanes 3,6) cells were probed with both the aBUSS double-stranded oligonucleotide of the same length (lanes 4–6). Auto-radiography revealed unique proteins detected by the aBUSS oligonucleotide for the HepG-2 and Caco-2 cells (lanes 1,2) that synthesize apoB and were not detected in the negative KB cell control (lane 3). The 23.5 and 25.4 kDa proteins were not detected by the irrelevant oligonucleotide (lanes 4,5).

In order to characterize the size of the proteins binding to aBUSS, Southwestern blotting was performed with Hep G2, Caco-2 and KB nuclear extracts. Unique protein species of 25.4 and 23.5 kDa were observed in the Hep G2 and Caco-2 extracts when they were probed with an end-labeled aBUSS oligonucleotide, but not with similarly sized irrelevant sequences (FIG. 6).

Homology searching of Genebank with the aBUSS sequence revealed no significant homologous regions with other 5′ flanking sequences. Of note was a 76% homology with a coding region of the mouse immunoglobulin gamma 2a-b gene, 89.5% homology with bases 6-24 of the aBUSS sequence and the varicella-zoster open-reading-frame 29, and a 100% homology with bases 1-15 of the aBUSS element and the *A. nidulans* never-in-mitosis mRNA, encoding a putative protein kinase.

These results demonstrate that regions of the apoB 5′ flanking sequence which are important for transcriptional regulation of apoB gene expression have been identified. A critical element for negative control of apoB transcription has been localized by transient transfection studies utilizing deletional analysis of the native apoB promoter as well as subsequent experiment with a heterologous promoter/reporter system. This element, located between -456 to -426 relative to the apoB transcriptional start, has been termed apoB upstream suppressor site (aBUSS). Additionally, unique tissue-specific trans-regulatory proteins which can bind to the aBUSS site have been identified in nuclear extracts from apoB producing cell lines (Hep G2 and Caco-2), but not non-apoB producing lines. Southwestern blotting has shown that these proteins have a molecular weight of approximately 23.5 and 25.4 kDa.

Figure 7:
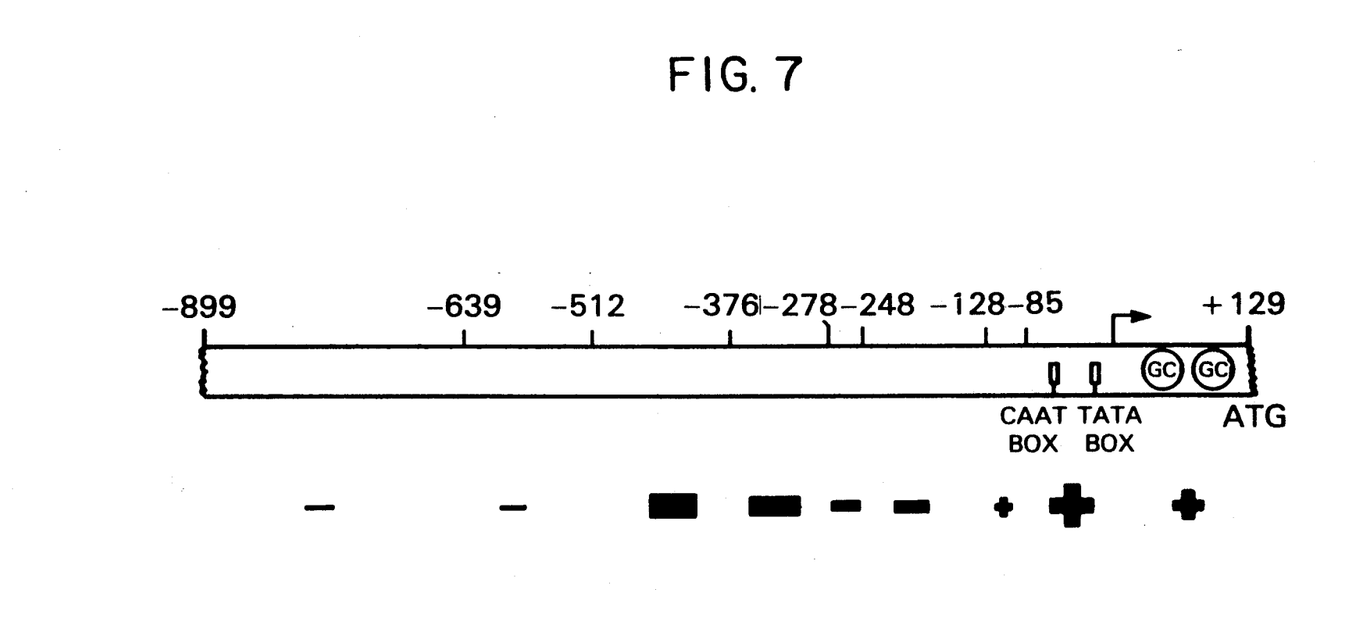
FIG. 7 presents the schematic summary of the important regulatory regions in the 5'-flanking sequence of the apoB gene. Important transcriptional regulatory sites including the start site, TATA and CAAT boxes, as well as GC-rich regions (i.e., putative SP1 binding sites) are indicated. The relative importance of each of these regions for apoB transcriptional regulation is indicated by the relative size of the plus or minus signs at each site.

Sequence specific binding proteins have only recently been found to be a critical control mechanism for eukaryotic gene expression (Maniatis et al, 1987, Science 236:1237-1244; Dynan and Tjian, 1985, Nature 316:774-777). The findings of the present invention lend support to this mechanism. Progressive 5′ to 3′ deletional analysis of the apoB 5′ flanking sequence revealed the presence of numerous negatively as well as positively acting sites. A summary of important regions in the apoB gene is diagrammed in FIG. 7. One of these regions, a 31 base pair element, has been demonstrated to be important for apoB transcriptional regulation. This cis-element, aBUSS, can induce negative control on a heterologous minimal promoter. In this heterologous system, the element is active directly upstream of the hsv/tk promoter when it is in the correct (i.e., that found in the native apoB gene), but not reverse orientation. These results implicate aBUSS as an important upstream negative promoter sequence. When the element is placed in the context of surrounding native apoB sequences (FIG. 5-plasmids E,F) it actively suppresses in the reverse orientation. These constructions both place aBUSS in the microenvironment of additional surrounding native apoB sequence, but also distance it 41 to 58 bases from the hsv/tk promoter depending upon the orientation of the fragment.

Potential tissue-specific trans-acting factors of 23.5 and 25.4 kDa which bind to the aBUSS site have been identified by Southwestern and gel mobility shift assays. The Southwestern blot established the two proteins which bind to the aBUSS oligonucleotide in both Hep G2 and Caco-2 nuclear extracts. The gel mobility shift assay revealed two bands corresponding to these two molecular species with the Hep G2 extract. Without being bound to any specific theory, it is postulated that this is most likely due to differences in binding the Caco-2 extract versus HepG2 extract to this region of the apoB gene. The broad footprint noted in the aBUSS region may, therefore, represent two overlapping or contiguous binding sites for these trans-acting factors. The present invention for the first time provides an element which can decrease the production of an atherogenic producing protein. Systems such as aBUSS and ARP may affect downregulation at the level of apolipoprotein transcription. Apolipoprotein B has been shown to be highly correlated with the risk for premature atherosclerosis, and the identification of this element provides a novel site for developing specific strategies to reduce the biosynthesis of apoB and the risk for developing atherosclerotic cardiovascular disease, such strategies being easily suggested to those skilled in the art to which this invention belongs.

A deposit of the cloned suppressor element (pSVO CAT) has been made at the ATCC, Rockville, Md. on Sep. 7, 1990 under the accession number 40885. The deposit shall be viably maintained, replacing if it becomes non-viable during the life of the patent for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A cloned cis-acting DNA sequence that mediates the suppression of atherogenic apolipoprotein B (apoB) transcription, consisting essentially of the following nucleotide sequence:

GCAAATCCAAGGTCCACCAAAATG-GAAAAGA

2. The cloned cis-acting DNA sequence of claim 1 being that which is deposited at the ATCC under accession number 40885.

* * * * *